United States Patent [19]

Doyle

[11] Patent Number: 5,983,898
[45] Date of Patent: Nov. 16, 1999

[54] AIRWAY SPLINT OBTURATOR

[76] Inventor: Donald E. Doyle, 4105 Hospital Rd, Pascagoula, Miss. 39581

[21] Appl. No.: 09/067,423

[22] Filed: Apr. 28, 1998

Related U.S. Application Data

[60] Provisional application No. 60/044,441, Apr. 30, 1997.
[51] Int. Cl.⁶ ............................. A61M 29/00; A67F 9/00
[52] U.S. Cl. ......................................... 128/858; 606/199
[58] Field of Search .................... 602/5, 17; 606/204.45, 606/199; 128/848, 858; 623/10; 604/94

[56] References Cited

U.S. PATENT DOCUMENTS

| Re. 35,408 | 12/1996 | Petruson | 128/858 |
| 1,256,188 | 2/1918 | Wilson | 606/199 |
| 3,935,859 | 2/1976 | Doyle | 606/196 |
| 4,592,357 | 6/1986 | Ersek | 606/199 |
| 4,818,320 | 4/1989 | Weichselbaum | 604/94 |
| 5,094,233 | 3/1992 | Brennan | 602/6 |
| 5,287,584 | 2/1994 | Skinner | 15/167.1 |
| 5,350,396 | 9/1994 | Eliacher | 602/5 X |

Primary Examiner—Richard J. Apley
Assistant Examiner—Denise Pothier
Attorney, Agent, or Firm—Roger A. Marrs

[57] ABSTRACT

A nasal splint obturator for maintaining splint passageways open and unblocked having a yoke-like device including spaced-apart and parallel arms joined by a cross member with a downwardly depending finger-grasping element. The arms are elongated of semi-circular cross-section having opposing inner flat surfaces and curved outer surfaces. In another version, a single elongated member is employed of hollow construction and including a finger hole adapted to be temporarily covered to permit evacuation by suction techniques.

3 Claims, 1 Drawing Sheet

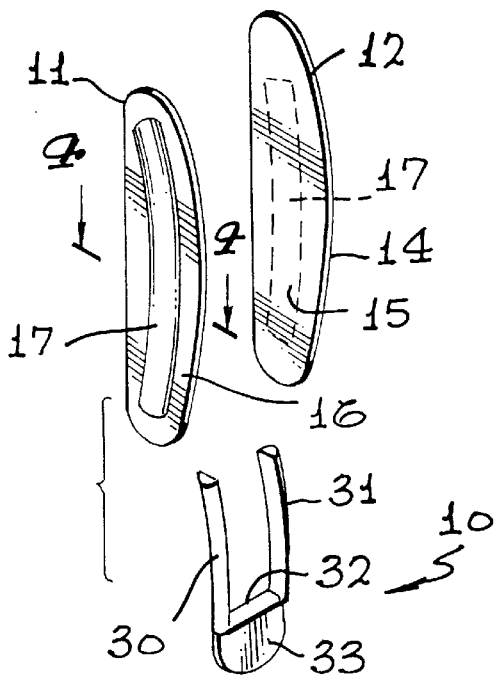
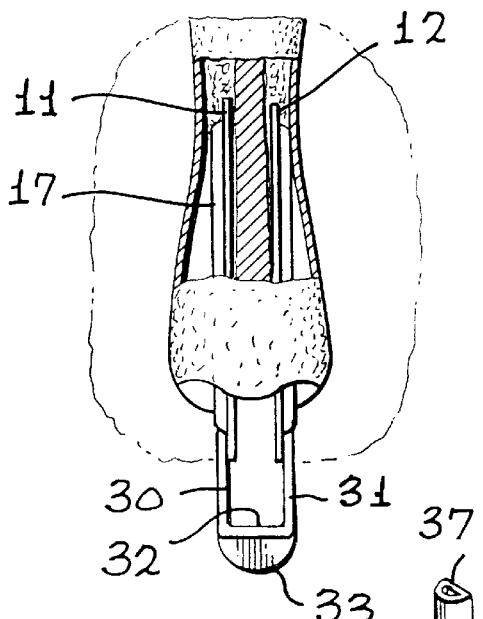
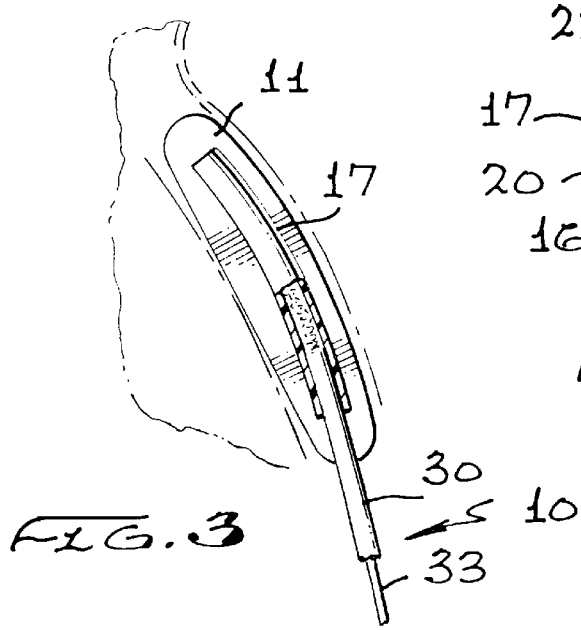
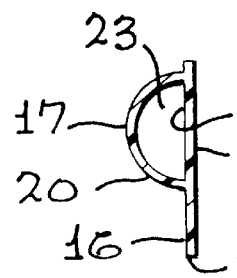
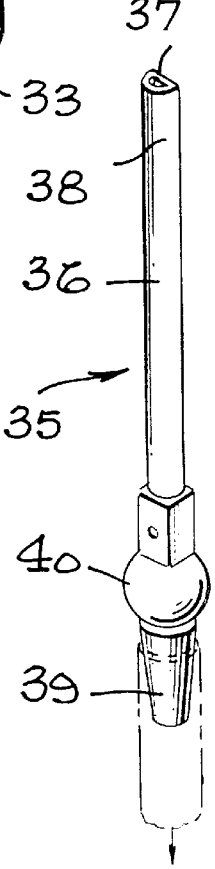

AIRWAY SPLINT OBTURATOR

Priority based on Ser. No. 60-044,441 filed Apr. 30, 1997

BACKGROUND OF THE INVENTION

1. Field of the Invention

The present invention relates to the field of medical devices, and more particularly to a novel means for maintaining the airway tubes or passageways in an intranasal splint free from clogging or blockage.

2. Brief Description of the Prior Art

In the past, it has been the conventional practice to employ a preformed intranasal splint with airway tubes or passageways formed therein that can be used by patients who have undergone surgery upon their nasal septum. The nasal septum is the partition between the left and rights sides of the nose. Particularly after an operation, the airways or passageways in the splint become clogged or form blockages due to mucous, blood or the like, and therefore, the patient is essentially miserable because of the experience of having to breathe through his mouth for a considerable period of time. The primary purpose of the airways or passageways is to permit breathing subsequent to a nasal operation in a normal manner through the nasal passageways. Therefore, unless the passageways are maintained open, the essential provision of nasal breathing is defeated.

Therefore, a long-standing need has existed to provide a device and means for maintaining the airways or passageways in a nasal splint open so as to permit the patient to breathe normally through the nose. Such a device must be simple and must be able to be insertably received within the splint airways and which will further permit use of a suction tube regardless of suction device shape or size.

SUMMARY OF THE INVENTION

Accordingly, the above problems and difficulties are avoided by the present invention which provides a device for maintaining airways and passageways open in a nasal splint and which will permit evacuation by means of a suction device which includes a nasal splint having an elongated curved passageway with open opposite ends so as to permit air to travel therethrough. A yoke-like device having a pair of spaced-apart arms joined by a cross member with a downwardly depending finger-grasping element is provided. The spaced-apart arms are each of a curve form so as to match the shape of the airways or passageways in the splint when the free ends of the arms are inserted through the openings of the passageways. Each of the arms includes opposing flat surfaces which conform to the shape of the splint adjacent the surfaces and curved back surfaces which match the curvature, in cross-section, of the airway passageways. In a similar configuration, the suction tube of a suction device includes a flat surface and a back curved surface matching the airway of a respective splint. Therefore, upon insertion of the arms of the yoke-like device into the respective open ends of the splint passageways, the passageways can be cleared of any substance which would clog or block the passageway. In a similar manner, the tube of the suction device can be inserted into each of the respective splint passageways for evacuating any blockage or clogging substances.

Therefore, it is among the primary objects of the present invention to provide a novel and simple means for maintaining the airways or passageways of a nasal splint open and free from blockage or clogging by post-operative substances.

Another object of the present invention is to provide a novel means for unclogging breathing passageways provided in a nasal splint by suctional evacuation or employing a wedging device.

Yet a further object of the present invention it to provide a plugging device which can be inserted into the passageways of a nasal splint which may be utilized to plug the passageways while there is some bleeding and excess mucuous discharge and which will protect the splint passageways from aspiration of these natural substances.

Yet another object of the present invention is to provide a stopper device that fits precisely into the airway tubes of a pair of nasal splints and which are bilaterally connected together to provide a center fingerpad for the thumb and forefinger of the user for insertion or removal from the passageways.

A further object of the present invention is to provide a small suction tube configured in the form of an airway or passageway of a nasal splint that is small enough for insertion into the respective passageways to unplug or unblock any plugging that might have occurred in the first few hours of post-operative healing.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a perspective view of the novel clearance device for an intranasal airway splint in accordance with the present invention;

FIG. 2 is a front view of the clearance device illustrated in use with a pair of intranasal airway splints;

FIG. 3 is a side elevational view, partly in section, of the clearance device partially inserted in the airway or air passageways of the splints;

FIG. 4 is an enlarged transverse cross-sectional view of an intranasal airway splint shown in FIG. 1 as taken in the direction of arrows 4—4 thereof; and FIG. 5 is a perspective view of a suction device used in clearing blockage from the passageways in an intranasal splint.

DESCRIPTION OF THE PREFERRED EMBODIMENT

Referring to FIG. 1, the novel intranasal airway splint clearing or unplugging device is illustrated in the general direction of arrow 10 and the device is used in connection with a pair of such splints which are identified by numerals 11 and 12. Intranasal airway splints are well known in the prior art and include a base member 14 having a flat surface 15 intended to be held to the nasal septum by stitching through the edge marginal region of the member 14 directly into nasal tissue. The outside surface, indicated by numeral 16, in connection with nasal splint 11 supports an air passageway, such as a curved tube 17. In FIG. 4, the air passageway 23 is illustrated as being open-ended and includes an outer curved back side, broadly identified by numeral 20, and a flat inner surface 21 provided on the member 11 and coextensive with outer surface 16. The air passageway used for breathing purposes is indicated by numeral 23. It is this passageway that normally will clog or become blocked after a nasal operation and such clogging or blocking requires unplugging in order for the person to breathe through the nasal passageway.

For the purpose of unplugging any clogs or blockage, the airway obturator/protector device 10 is employed for clearing the passageways and such clearance can be achieved through both airways or passageways of splints 11 and 12 simultaneously. The device 10 includes a pair of arms 30 and 31 which are arranged in fixed spaced-apart relationship and are connected together at one end by a cross member 32. Downwardly depending from the cross member 32 is a finger-grasping flat surfaced element 33 so that the overall configuration of the device 10 appears to be yoke-like. It is important to note that the plane of the element 33 is parallel with the plane of the cross member 32 so that the opposite ends of the elongated and flat surfaced element 33 terminate adjacent the opposite ends of the cross member 32.

FIG. 1 also illustrates that the outside surface of each of the respective arms 30 and 31 are curved so as to match the curvature of the tube 17 or passageway 23 and such curvature is indicated by numeral 20. The inside surfaces of each arm 30 and 31 include a flat inner surface which matches with the flat surface 21 of the passageway 23 of each of the respective tubes or passageways carried on splints 11 and 12. Therefore, the cross-section of each arm 30 and 31 matches the shape and size of each passageway 23 of each of the respective splints. Therefore, upon insertion of the free ends of the arms 30 and 31 into the respective airways or passageways, further urging of the inserted arms will clear any blockage from the passageways. Furthermore, the device 10 may be left in the passageways for several hours after an operation so that clogging or blockage will not occur. Subsequently, the device can be removed by the user by grasping the element 33 between the thumb and index finger and extracting the device from the splint passageways.

Referring now in detail to FIG. 3, it can be seen that the clearance or plugging device 10 is partially inserted into the splint passageways, primarily passageway 23 of tube 17, and that the curvature of the tube 17 is followed by the curvature of the arms 30 and 31. The grasping element of the occluding device 10 is on the same plane as the passageways and the passageways as well as the arms 30 and 31 have some curvature to allow for the shape of a patient's nose externally. If the device were straight externally of the passageways in the tubes, it would appear to impinge upon the apices of each nostril. Therefore, a downward curve is needed.

Referring now in detail to FIG. 5, a suction device is indicated in the direction of arrow 35 which includes an elongated tube 36 having a cross-section similar to the cross-section of passageway 23, as shown in FIG. 4. To this end, tube 36 has a flat surface 37 and a back rounded or curved surface 38. The proximal end of the suction device 35 is circular and tapered, as represented by numeral 39. By this configuration, a variety of suction devices or tubes or hoses may be accommodated. The end 39 is placed into a suction tube and it tapers from a wide diameter at the top which narrows to its free end in order that the end may fit into and be accommodated by various suction tubes. The dimensions of not only the obturator device 10 but also the working end 39 of the suction device are critical. They must fit easily into an airway tube of an intranasal airway splint and totally occupy the cross-sectional diameter of the passageway in order to provide for adequate suction and blockage control. The main thrust of Applicant's invention is to (1) maintain the airway tube from collecting blood and/or mucous in the early post-operative hours and then (2) provide for a suction device which will be maximally effective to cleansing the tube. A ball-shaped portion 40 of the suction device 35 is a non-compressible member and is spheroidal in shape.

In view of the foregoing, it can be seen that the device of the present invention concerns the avoidance of clogging or blockage in the passageways of an intranasal airway splint. Such clogging or plugging generally occurs in the first few hours or within a day of the post-operation procedure. Therefore, the device of the present invention serves as a stopper device which precisely fits into the airway tubes bilaterally connected to a central finger element 33 for accommodating the thumb and forefinger of the user. The device is employed to occupy the passageways of the tubes on the respective nasal splints 11 and 12 while there is some bleeding and excess mucous discharge and the inventive device protects the tubes from aspiration of these materials. Then, a few hours or either the next morning after the postoperative procedure, the device including the arms 30 and 31 are removed by the recovery room team or by the patient himself. A further procedure provides for the placement of peroxide into the tubes at a subsequent time and then suctioning out the airway vents in order to reestablish nasal breathing. The suction tube 36 must have the precise dimensions and configuration to fit into the tube, such as tube 17, without tugging on the device itself and causing discomfort. Both the passageway 23 and the cross-section of tube 36 as well as arms 30 and 31 are essentially D-shaped.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A nasal splint obturator for maintaining passageways of a nasal splint open and free from blockage by post-operative substances comprising:

a pair of nasal splints with each splint having an elongated curved passageway;

a pair of elongated members with each member having opposite ends;

a selected end of said opposite ends of said elongated member connected by a flat cross member and a non-selected end of said opposite ends terminating in a flat surface;

said pair of elongated members being removably insertable into said elongated curved passageways of said pair of nasal splints;

each of said elongated members having a semi-circular cross-section along its length with an end flat surface and a curved surface extending between said selected and said non-selected ends;

a finger-engaging portion downwardly depending from said cross member;

said elongated members, said cross member and said finger-engaging portion are composed of a rigid and non-flexible material;

each of said elongated members is outwardly curved from said cross member along its length in parallel spaced-apart relationship with respect to each other; and said elongated member having a matching curvature with said curved passageway.

2. A nasal splint obturator for maintaining curved passageways of a nasal splint open and free from blockage by post-operative substances comprising:

a pair of nasal splints with each splint having an elongated curved passageway;

a yoke member having a cross bar of a fixed over-all length with opposite ends and each end of said opposite ends integrally supporting an elongated, curved member at each of said respective opposite ends;

said elongated, curved members arranged in fixed parallel spaced-apart relationship;

a flat surface-grasping portion downwardly depending from said cross bar;

said elongated, curved members outwardly projecting from a first side of said cross bar and said finger-grasping portion projecting from a second side of said cross member;

each of said elongated, curved members having a semicircular cross-section throughout its length with inner flat surfaces of each elongated, curved member facing each other in spaced-apart opposing relationship and each of said elongated, curved members having a curved surface;

said finger-grasping portion having an overall length shorter than said overall length of said cross bar; and said elongated, curved members of semicircular cross-section are removably insertable into the curved passageways of the nasal splints and said elongated members having a matching curvature with said curved passageway.

3. In a nasal splint obturator for maintaining a curved, open-ended passageway of a nasal splint open and free from blockage by post-operative substances wherein said passageway is semicircular in cross-section, the improvement with comprises:

an elongated member having an internal passage defined by a surrounding structure of semicircular cross-section throughout its length with a flat surface and a semicircular surface;

said elongated member being a suction device removably insertable into said curved, open-ended passageway; and said elongated member having a matching curvature with said curved open-ended passageway.

* * * * *